United States Patent

Cooke et al.

[11] 4,429,162
[45] Jan. 31, 1984

[54] PERFLUOROALKYL PHENOLS AND NAPHTHOLS

[75] Inventors: Thomas W. Cooke, Mahopac; Robert A. Falk, New City, both of N.Y.

[73] Assignee: Ciba-Geigy Corporation, Ardsley, N.Y.

[21] Appl. No.: 344,681

[22] Filed: Feb. 1, 1982

[51] Int. Cl.$^3$ .................. C07C 149/36; C07C 149/42
[52] U.S. Cl. .......................... 568/50; 260/505 R; 260/508; 260/509; 260/510; 260/512 R; 544/158; 544/159; 546/206; 546/232; 546/236; 546/240; 546/334; 546/339; 546/344; 564/280; 564/287; 564/317; 564/340; 568/29; 568/36; 568/40; 568/45
[58] Field of Search .................. 568/29, 36, 40, 46, 568/47, 51, 52, 45, 49, 50; 564/280, 287, 317, 340

[56] References Cited

U.S. PATENT DOCUMENTS 3,821,334  6/1974  Schmidt et al. .................. 568/33
3,917,714  11/1975  Richmond ........................ 568/33
4,239,915  12/1980  Falk ............................ 562/481

*Primary Examiner*—Donald G. Daus
*Assistant Examiner*—M. C. Eakin
*Attorney, Agent, or Firm*—Michael W. Glynn

[57] ABSTRACT

The instant invention relates to compounds of the formula

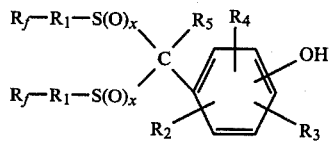

wherein
each $R_f$ is independently straight or branched chain perfluoroalkyl of 2 to 18 carbon atoms or perfluoroalkoxy-perfluoroalkyl of 4 to 18 carbon atoms;
each $R_1$ is independently straight or branched chain alkylene of 1 to 12 carbon atoms, alkylenethioalkylene of 2 to 12 carbon atoms, alkyleneoxyalkylene of 2 to 12 carbon atoms, or alkyleneiminoalkylene of 2 to 12 carbon atoms where the imino nitrogen atom contains as a third substituent, hydrogen or alkyl of 1 to 6 carbon atoms;
$R_2$, $R_3$ and $R_4$ are independently hydrogen, chloro, bromo, alkyl of 1 to 6 carbon atoms, alkenyl of 2 to 6 carbon atoms, hydroxyalkyl of 1 to 6 carbon atoms or alkoxy of 1 to 6 carbon atoms, and $R_2$ and $R_3$ additionally may, together with the carbon atoms to which they are attached, form a fused benzo ring;
$R_5$ is hydrogen, or alkyl of 1 to 6 carbon atoms which is unsubstituted or substituted by hydroxy, alkoxy of 1 to 6 carbon atoms or phenyl;
x is 0, 1 or 2; and the alkali metal, alkaline earth metal, ammonium or amine salt thereof. These compounds are useful as surfactants, water repellents and intermediates.

9 Claims, No Drawings

PERFLUOROALKYL PHENOLS AND NAPHTHOLS

BACKGROUND OF THE INVENTION

This invention is directed to perfluoroalkyl group containing phenols, and salts thereof. These compounds are useful as surfactants, water repellents and intermediates.

Compounds of the type

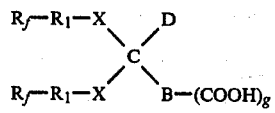

where $R_f$ is perfluoroalkyl, $R_1$ is alkylene or alkylthio- or -oxy- or -imino-alkylene, D is hydrogen, alkyl or phenyl, B is a covalent bond, alkylene or alkanetriyl and g is 1 or 2, are known from U.S. Pat. No. 4,239,915. Such compounds, while highly useful in themselves as surfactants, oil and water repellents and the like, do not contain the requisite hydroxyaryl group of the instant compounds. The polar phenolic and naphtholic hydroxy group on the instant inventive compounds are highly advantageous. Not only are the phenate and naphtholate salts surface active, but they react readily, for example, with halo alkanoic acids to form the corresponding phenoxy- and naphthoxy-alkanoic acids. Moreover, the phenols and naphthols of the instant invention react with polybasic acids, such as sulfuric acid and phosphoric acid, to form the corresponding hemi-esters or with haloalkylammonium compounds to form the corresponding oxyalkylammonium salts having highly advantageous surfactant and oil and water repellent properties. Other useful derivatives are readily apparent to the artisan.

It is therefor an object of the instant invention to provide new and useful perfluoroalkyl phenols and naphthols.

It is a further object of the instant invention to provide a method of producing such perfluoroalkyl phenols and naphthols.

It is a further object of the instant invention to provide useful derivatives of such perfluoroalkyl phenols and naphthols.

DETAILED DESCRIPTION OF THE INVENTION

The perfluoroalkyl phenols and naphthols of this invention have the general formula

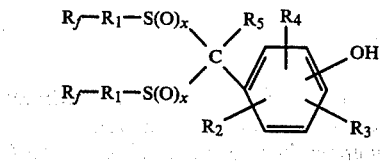

wherein
  each $R_f$ is independently straight or branched chain perfluoroalkyl of 2 to 18 carbon atoms or perfluoroalkoxy-perfluoroalkyl of 4 to 18 carbon atoms;
  each $R_1$ is independently straight or branched chain alkylene of 1 to 12 carbon atoms, alkylenethioalkylene of 2 to 12 carbon atoms, alkyleneoxalkylene of 2 to 12 carbon atoms, or alkyleneiminoalkylene of 2 to 12 carbon atoms where the imino nitrogen atom contain as a third substituent, hydrogen or alkyl of 1 to 6 carbon atoms;
  each $R_2$, $R_3$ and $R_4$ are independently hydrogen, chloro, bromo, alkyl of 1 to 6 carbon atoms, hydroxyalkyl of 1 to 6 carbon atoms or alkoxy of 1 to 6 carbon atoms, and $R_2$ and $R_3$ additionally may, together with the carbon atoms to which they are attached, form a fused benzo ring;
  $R_5$ is hydrogen, or alkyl of 1 to 6 carbon atoms which is unsubstituted or substituted by hydroxy, alkoxy of 1 to 6 carbon atoms or phenyl;
  x is 0, 1 or 2; and
  the alkali metal, alkaline earth metal, ammonium or amine phenate salts thereof.

Suitable salts include, for example, the sodium, lithium and potassium alkali metal salts, and the magnesium, calcium, strontium and barium alkaline earth metal salts.

Suitable ammonium and amine salts include those wherein the cation has the formula

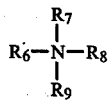 (Ia)

where
  $R_6$, $R_7$ and $R_8$ are independently hydrogen, alkyl of 1 to 5 carbon atoms, hydroxyalkyl of 2 to 5 carbon atoms, ethyleneoxyethanol or polyethyleneoxyethanol having 2 to 20 ethyleneoxy units; and
  $R_9$ is hydrogen, alkyl of 1 to 23 carbon atoms, hydroxyalkyl of 2 to 5 carbon atoms, phenyl, benzyl, cyclohexyl, ethyleneoxyethanol or polyethylenoxyethanol having 2 to 20 ethyleneoxy units.

Suitable salts of this type include, without limitation, the ammonium salt and salts of conventional amines such as the methylamine salt, dimethylamine salt, trimethylamine salt, tetramethylamine salt, ethylamine salt, ethanolamine salt, diethylamine salt, diethanolamine, triethanolamine salt, triethylamine salt, tetraethanolamine salt, tributylamine salt, aniline salt, benzylamine salt, cyclohexylamine salt, tributylamine salt, bis(2-hydroxypropyl) amine salt, and bis(2-hydroxyethyl) coco amine salt, and the like.

Preferred compounds of this invention are those of formula I where
  $R_f$ is perfluoroalkyl of 4 to 12 carbon atoms;
  $R_1$ is alkylene of 2 to 6 carbon atoms;
  $R_2$ and $R_3$ are hydrogen;
  $R_4$ is hydrogen, alkyl of 1 to 4 carbon atoms or alkoxy of 1 to 4 carbon atoms;
  $R_5$ is hydrogen or alkyl of 1 to 4 carbon atoms;
  x is 0, 1 or 2;
and the alkali metal, alkaline earth metal, ammonium or amine phenate salts thereof.

Particularly preferred are those compounds of formula I where $R_f$ is perfluoroalkyl of 6 to 12 carbon atoms, $R_1$ is alkylene of 2 to 4 carbon atoms, $R_2$ and $R_3$ are hydrogen, $R_4$ is hydrogen, alkyl of 1 to 2 carbon atom, or alkoxy of 1 to 2 carbon atoms, $R_5$ is hydrogen or alkyl of 1 to 2 carbon atoms, x is 0, 1 or 2, and the alkali metal, alkaline earth metal, ammonium or amine phenate salts thereof.

An especially preferred group are those compounds of the formula

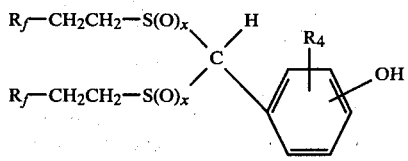

where $R_f$ is perfuoroalkyl of 6 to 12 carbon atoms, x is 0, 1 or 2, and $R_4$ is hydrogen, methyl or methoxy.

The perfluoroalkyl containing phenols and naphthols of the present invention, where x equals 0, are conveniently prepared by reacting a perfluoroalkyl containing mercaptan of the formula

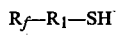

with an aromatic aldehyde or ketone of the formula

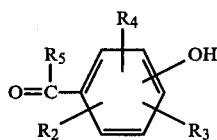

according to the reaction:

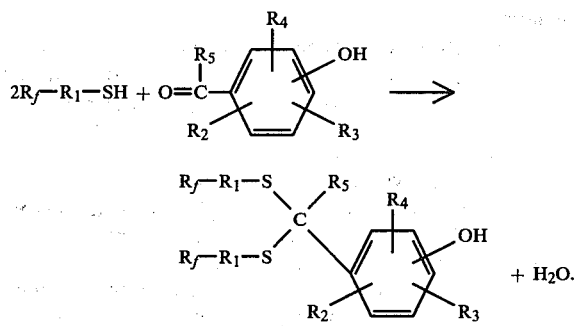

The reaction is catalyzed through the use of an acid catalyst. The preferred catalyst recommended is anhydrous hydrogen chloride, although concentrated hydrochloric acid, boron trifluoride, zinc chloride, paratoluene sulfonic acid and other Lewis acids may be used.

Stoichiometric amounts of reactants are advantageously employed, i.e., 2 moles of mercaptan per mole of aldehyde or ketone, but an excess of mercaptan may be employed, if desired, to assist in driving the reaction to completion. The reaction can be performed neat, or in the presence of a solvent. Suitable solvents include glacial acetic acid, aliphatic and aromatic hydrocarbons such as heptane, benzene, toluene, etc.; halogenated hydrocarbons such as methylene chloride, chloroform, methyl chloroform, carbon tetrachloride, trichloroethylene, perchloroethylene, 1,1,2-trifluoro-1,2,2-trichloroethene, and chlorobenzene; esters, such as ethyl acetate; ethers such as tetrahydrofuran, ethyleneglycol dimethyl or diethyl ether, and the like. The reaction temperature is advantageously between room temperature and 100° C.

The required reaction times depend upon the reaction temperature, mole ratio of reactants, compound reactivities and the nature of the acid catalyst used, and may range from about 5 minutes to a week. The products can be isolated from the reaction medium by filtration or evaporation of solvent and catalyst and may be purified by employing crystallization, precipitation or distillation.

Those perfluoroalkyl containing phenols and naphthols where x is 1 or 2, i.e. the sulfoxides and sulfones, may be advantageously prepared by reacting the corresponding perfluoroalkyl containing phenols and naphthols where x is 0, with a suitable oxidizing agent such as potassium persulfate, peracetic acid, performic acid, metachloroperoxybenzoic acid, potassium permanganate and hydrogen peroxide. Metachloroperbenzoic acid is the preferred oxidizing agent. Advantageously 2 moles of metachloroperbenzoic acid are reacted per mole of bis perfluoroalkyl thioether at about 40° to 50° C. to obtain the corresponding sulfoxide derivatives, i.e. where x is 1, and 4 moles of metachlorobenzoic acid is reacted per mole of bis perfluoroalkyl thioether at about 90° to 100° C. to obtain the corresponding sulfone derivatives, i.e. where x is 2. An excess of oxidizing agent may be also used under controlled temperature conditions. Thus, at lower temperatures, such as 30° to 60° C., the formation of the sulfoxide derivative predominates, while at higher temperatures, such as 90° to 100° C., the sulfone derivative is preferentially produced.

The perfluoroalkyl containing phenols and naphthols of formula I and the salts thereof can be reacted with haloalkanoic acids, especially halo-(lower)alkanoic acids, to form the corresponding phenoxy- or naphthoxy-alkanoic acids and their alkali metal, alkaline earth metal, ammonium and amine salts thereof. The reaction is advantageously conducted in an inert solvent or diluent such as ethanol, isopropanol or the like. Where the starting material of formula I is in the form of the free acid, a base, such as sodium hydroxide, potassium hydroxide and the like, is advantageously added in an amount of one to ten moles per mole of said free acid. The reaction conditions are ordinarily between about 0° C. and 100° C., preferably between 30° C. and 80° C. The resulting phenoxy- and naphthoxy-alkanoic acid salts, especially the diethanolamine salts, are useful in the form of their aqueous emulsions, as internal and external paper sizing agents to render the same water and oil repellant. They are also useful as surfactants in aqueous and organic media.

Alternatively the perfluoroalkyl containing phenols and naphthols of formula I can be reacted with haloalkylammonium compounds of the formula

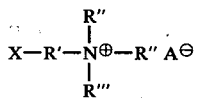

wherein
X is chloro, bromo or iodo;
R' is alkylene of 1 to 6 carbon atoms or hydroxy substituted alkylene of 3 to 6 carbon atoms;
each R" is independently hydrogen or alkyl 1 to 4 carbon atoms, or together with the nitrogen to which they are attached, represent piperidino or morpholino;
R''' is hydrogen, alkyl of 1 to 4 carbon atoms or benzyl, or together with each R" and the nitrogen to which they are attached, represents pyridyl; and
A represents an anion equivalent, to form the corresponding fluoroalkyl containing phenoxy- or naphthoxy-alkyl ammonium compound of the formula

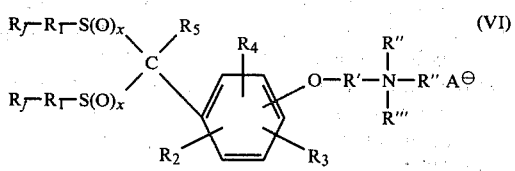

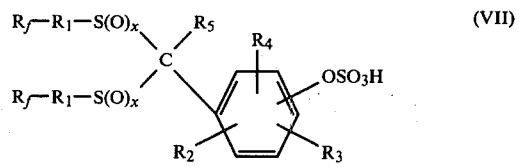

where $R_f$, $R_1$, $R_2$, $R_3$, $R_4$, $R_5$, $X$, $R'$, $R''$, $R'''$ and $A$ are as defined above.

Preferred anions, $A^\ominus$, are the halo anion, especially chloro and bromo, the sulfate anion, the lower alkyl sulfate anion, especially methylsulfate, the lower alkanoate anion, especially acetate, and the lower alkylsulfonic acid, especially the methylsulfonate and ethylsulfonate.

Preferably $R'$ is alkylene of 2 to 4 carbon atoms or hydroxy substituted alkylene of 3 to 4 carbon atoms, $R''$ is alkyl of 1 to 4 carbon atoms, and $R'''$ is alkyl of 1 to 4 carbon atoms.

Particularly preferred compounds are those of formula VI wherein $R_f$ is perfluoroalkyl of 6 to 12 carbon atoms, $x$ is 0, 1 or 2, $R_1$ is ethylene, $R_2$ and $R_3$ are hydrogen, $R_4$ is hydrogen, alkyl of 1 to 2 carbon atoms or alkoxy of 1 to 2 carbon atoms, and $R_5$ is hydrogen or alkyl of 1 to 2 carbon atoms.

Especially preferred are those compounds of formula VI wherein $R_f$ is perfluoroalkyl of 6 to 12 carbon atoms, $R_1$ is ethylene, $R_2$ and $R_3$ are hydrogen, $R_4$ is hydrogen methyl or methoxy, and $R_5$ is hydrogen.

The compounds of formula I are reacted with the haloalkyleneammonium compounds of formula V to form the derivatives of formula VI preferably in the presence of an inert or solvent, such as ethanol or isopropanol at a temperature between about 0° C. to 100° C., preferably between 30° C. and 85° C. Where the starting material of formula I is in the form of the free phenol or naphthol, a base, such as sodium hydroxide or potassium hydroxide, is advantageously added in an amount of one to two moles per mole of phenol or naphthol.

The compounds of formula VI are useful as cationic surfactants in aqueous media and in the form of aqueous solutions or emulsions, as internal and external paper sizing agents to render the same water and oil repellant.

Similarly, the compounds of formula I can be reacted with polybasic acids, such as sulfuric acid, phosphoric acid, or derivatives thereof, to form the corresponding hemi-esters, useful as surfactants and paper sizing agents to render them oil and water repellent.

In an embodiment the compounds of formula I, in the form of the free phenol or naphthol, are reacted with sulfamic acid in the presence of a tertiary amine, such as triethylamine or pyridine, at a reaction temperature between about 30° C. and 120° C. in the presence or absence of an inert diluent, to form the corresponding hemisulfate ester ammonium salt. If desired, the ammonium cation may be replaced by an alkali metal, alkaline, earth metal or amine cation, eg. by conventional ion exchange techniques. The hemisulfate ester derivatives have the formula wherein $R_f$, $R_1$, $R_2$, $R_3$, $R_4$, $R_5$ and $X$ have the aforementioned meanings, and the alkali metal, alkaline earth metal, ammonium or amine salt thereof. The preferred ammonium and amine salts are those wherein the cation is that of formula (Ia), above. The preferred embodiments of $R_f$, $R_1$, $R_2$, $R_3$, $R_4$ and $R_5$ correspond to the preferred embodiments of formula I, and the especially preferred compounds are those hemisulfate esters, and salts thereof, of the phenols of formula II.

The compounds of formula VII and their salts are useful as surfactants, and in the form of their aqueous solutions or emulsions, are especially useful as external and internal paper sizing agents, to render the same oil and water repellent.

In using various derivatives of the instant intermediate phenols of formula I as external and internal paper sizing agents, it is advantageous to use the techniques and methods described in copending application Ser. No. 292,326, filed Aug. 12, 1981, incorporated in toto by reference herein.

The following examples are intended for illustrative purposes only, and are not intended to restrict the scope of the invention in any way. All parts are by weight unless otherwise specified.

EXAMPLE 1

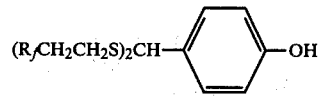

A 1000 ml. 3-neck round bottom flask on a heating mantle was equipped with a mechanical stirrer, thermometer and below liquid level gas inlet tube. Into the flask were introduced 12.21 g (0.10 moles) p-hydroxybenzaldehyde, 120.4 g. (0.20 moles) $R_fCH_2CH_2SH$ wherein the $R_f$ distribution was n-$C_6F_{13}$=2.3%, n-$C_8F_{17}$=6.6%, n-$C_{10}F_{21}$=68.6%, n-$C_{12}F_{25}$=17.9% and $C_{14}F_{29}$=1.4%, and 500 g. glacial acetic acid, and stirred at 50° C., forming a clear yellow solution. The heating mantle was then removed and anhydrous HCl was bubbled into the reaction mixture. The temperature rose to 56° C. The HCl was bubbled in for a total of 2½ hours at about 50°-52° C. The reaction mixture became dark amber with some solids forming. The reaction was continued at 50° C. for a total of about 20 hours. The molten product was then precipitated into 2 liters of distilled water with stirring. The product was filtered and dried at 60°-70° C., first in a draft oven and then in a vacuum oven. The solids were pulverized into a light pink powder (116.7 g. collected=88.0% yield).

Analysis for $C_{31}F_{42}H_{14}S_2O_1$: calc.; C 29.4, H 1.1, F 63.1, OH(titration) 1.3. found; C 29.96, H 1.2, F 63.57, OH(titration) 1.47.

$^1$H-NMR spectrum 2.4-3.0 ppm, 5.35 ppm, 6.85 ppm, 7.2 ppm, 8.30 ppm in a ratio of approx. 8:1:2:2:1.

EXAMPLE 2

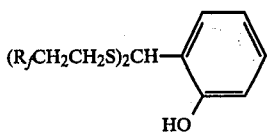

Into a 500 ml. 3-neck round bottom flask fitted with a mechanical stirrer, thermometer, condenser and $N_2$ inlet on a steam bath was added 117.67 g. (0.252 moles) $R_fCH_2CH_2SH$ having an $R_f$ distribution of n-$C_6F_{13}=1.7\%$, n-$C_8F_{17}=94.3\%$ and n-$C_{10}F_{21}=1.3\%$, 14.66 g. (0.120 moles) salicylaldehyde, 113.03 g. toluene and 11.53 g (0.120 moles) methane sulfonic acid. A slight exotherm was noticed presumably from the methane sulfonic acid addition, which was controlled by the bath. The solution was dark red after the methane sulfonic acid addition. The reaction mixture was stirred at 65° C. for 1½ hours. The solution was then poured out into about 400 ml. of distilled water in an ice bath. A pink foam dispersion resulted. The toluene/water mixture was removed from the reaction product by stripping in a Buchi rotary evaporator, resulting in pinkish-white chunks of reaction product solids, which were dried in a draft oven at about 45° C. (yield=61%).

Analysis for $C_{27}H_{14}F_{34}OS_2$: calc.; C 31.21, H 1.35, F 62.23. found; 30.3, H 1.7, F 45.4.

EXAMPLE 3

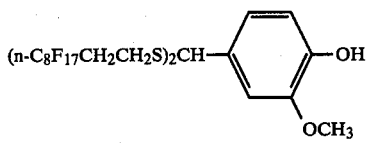

Into a 500 ml 3-neck round bottom flask were charged 15.2 g. (0.1 moles) vanillin (99% pure), 96 g. (0.2 moles) n-$C_8F_{17}CH_2CH_2SH$, 70 ml. toluene and 30 ml. glacial acetic acid. HCl gas was introduced and the temperature rose to about 40° C. The reaction mixture was heated to 50°–60° C. for 1½ hours with further bubbling in of HCl gas. The reaction mixture was then cooled, washed with ice-water and filtered. The filter cake was washed twice with a 1:1 mixture of water/methanol. After drying in a vacuum oven, the white reaction product powder weighed 108 g (yield=98.7%).

Analysis for $C_{28}H_{16}F_{34}O_2S_2$: calc.; C 30.71%, H 1.4%, F 59.05%, S 5.85%. found; C 30.50%, H 1.48%, F 57.38%, S 6.41%.

'H-NMR Spectrum: 1.85-3.27 ppm, 3.87 ppm, 4.94 ppm, 6.99-7.10 ppm in a ratio of approx 8:3:1:1:3.

EXAMPLE 4

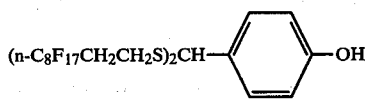

Into a 500 ml 3-neck round bottom flask were charged 12.4 g (0.102 moles) p-hydroxybenzaldehyde, 96 g (0.199 moles) n-$C_8F_{17}CH_2CH_2SH$, 5.0 ml toluene and 25 ml acetic acid. HCl gas was introduced and the temperature rose to 50° C. With additional heating to 50°–60° C., HCL gas was further bubbled through the reaction mixture for 1½ hours. The reaction product was then cooled, washed with ice water and filtered. The filter residue was dried in an oven to yield a pink product which weighed 33 g (yield=31.2%) and having a melting point of 56°–59° C. The product was further washed with a 1:1 methanol/water and then pure methanol, resulting in a product having melting point of about 59° C.

Analysis for $C_{27}H_{14}F_{34}OS_2$: calc.; C 30.45%, H 1.32%, F 60.71%, S 6.02%. found; C 30.49%, H 1.50%, F 57.77%, S 6.57%.

'H-NMR Spectrum: 7.34-3.34 ppm (singlet and complex, respectively), 4.91 ppm(s), 6.80+7.31 ppm (AA'BB') in a ratio of 1:8:1:4.

EXAMPLE 5

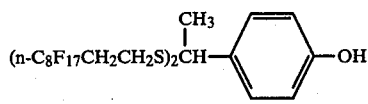

Into a 500 ml 3-neck round bottom flask were charged 13.6 g (0.1 moles) p-hydroxyacetophenone, 96.0 g (0.2 moles) n-$C_8F_{17}CH_2CH_2SH$, 100 ml toluene and 25 ml glacial acetic acid, and the mixture was heated for 4 hours to 50°–55° C. The acetic acid and toluene were evaporated from the reaction product.

Analysis for $C_{28}H_{16}F_{34}OS_2$ (after washing with 1.1 mixture of methanol/water): calc.; C 31.17%, H 1.48%, F 59.93%, S 5.94%. found; C 25.69%, H 1.18%, F 60.41%, S 7.10%.

The product is soluble in toluene and acetone and only slightly soluble in dimethyl sulfoxide.

EXAMPLE 6

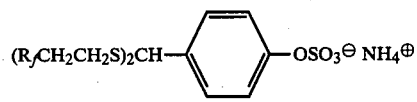

Into a 250 ml. erlenmeyer flask fitted with a magnetic stirrer and reflux condenser on a hot-plate were placed 18.98 g. (0.0150 moles) of the product of Example 1, 1.60 g. (0.0165 moles) sulfamic acid and 50 g. pyridine. The reaction mixture was stirred and slowly heated (about ½ hour) to reflux. After refluxing for about 5 minutes, with some foaming, the reaction product was slowing cooled. The contents were then removed from the flask and evaporated to solids at 60° C. in a vacuum oven (about 40 mm Hg.) overnight. The resulting orange-amber solids were recrystallized from 500 ml. dry acetone by chilling and filtration. The product was dried in a 60° vacuum oven at about 0.2 mm. 11.4 g (55.8% yield) of a yellow orange powder was collected.

EXAMPLE 7

An emulsion was prepared from 9.0 grams of the product of Example 6 and 18.0 grams of Cellosolve by warming then adding 17.0 grams water, 0.6 grams Tetronic 701 and 0.4 grams Tetronic 504 emulsifiers, and homogenized. Then 18.0 grams of water were added. and the product was again homogenized. A viscous opaque-orange emulsion resulted containing 18.2% solids. This emulsion is useful in rendering paper articles both hydrophobic and oleophobic by applying the emulsion to the paper article and drying the treated paper article.

EXAMPLE 8

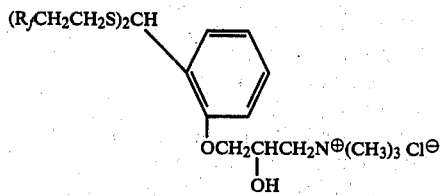

Into a 300 ml round bottom, 3-neck flask fitted with a mechanical stirrer, thermometer, $N_2$-inlet and reflux condenser were placed 15.57 g (0.0150 moles) of the product of Example 2, 100 g. isopropanol, and 5.68 g (0.0155 moles) of N-(3-chloro-2-hydroxypropyl) N,N,N-trimethyl ammonium chloride (51.3% actives) and stirred while heated to 75° C. A pale pink clear solution resulted. Then 1.24 (0.0155 moles) of 50% aqueous sodium hydroxide was added with stirring. A white NaCl precipitate immediately formed. The system was stirred for an additional ½ hour at 75° C. The hot contents of the flask were then transferred to a pressure filter and filtered through a 2-4 micron pad. The resulting clear, almost colorless solution was dried in a 50° C. draft oven for 3 days followed by room temperature storage in vacuum apparatus. 16.2 g. of a very slightly pink wax-like solid was collected (90.8% yield).

Analysis for $C_{33}F_{34}H_{28}O_2S_2NCl$: calc.; C 32.60%, H 2.32%, N 1.15%, F 53.11%. found; C 35.5%, H 3.3%, N 1.5%, F 44.5%.

'H NMR spectrum: 2.00-3.10 ppm (b. complex), 3.32 ppm(s), 6.60-8.00 ppm (b. complex) in a ratio of about 8:9:4.

EXAMPLE 9

2 g. of the product of Example 8 were mixed with 0.20 g. of Pluronic F-68 and 17.80 g. isopropanol and the mixture was warmed with stirring until all the solids dissolved. The weight of the product solution was readjusted to 20 grams by addition of isopropanol to obtain a hazy solution. 2 g. of this solution were then added to 20 cc of isopropanol and diluted to 100 ml by addition of distilled water. The diluted solution was then used as an internal fluorochemical sizing agent for paper pulp to render the same oil and water repellent, by adding 100 ml of the diluted solution to 6 g. of dry pulp admixed with 300 g. water.

EXAMPLE 10

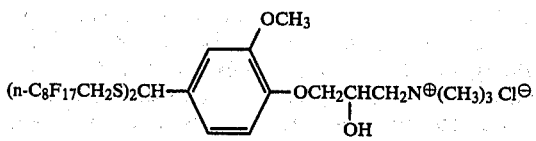

Into a 500 ml erlenmeyer flask containing a magnetic stirrer, Claissen adapter with $N_2$-inlet and condenser, in a temperature controlled bath, there was added 16.41 g (0.0150 moles) of the product of Example 3, 100 g. isopropanol and 5.68 g (0.0155 moles) of N-(3-chloro-2-hydroxypropyl)N,N,N-trimethyl ammonium chloride (51.3% actives in water) and stirred while heated to 75° C. To the resulting solution 1.24 g (0.0155 moles) of 50% aqueous sodium hydroxide was added with stirring. A precipitate of NaCl formed and the system was stirred for an additional ½ hour at 75° C. The product was filtered and the filtrate, which was almost colorless and clear, was stripped down in a rotary evaporator. The product was dried further in a 55° C. draft oven overnight. 18.8 g of a light amber spongy product was collected (100.6% yield). When cooled to room temperature, the amber spongy material was ground to a beige powder.

Analysis for $C_{34}H_{30}F_{34}O_3S_2NCl$: calc.; C 32.77%, H 2.42%, N 1.12%, F 51.83%. found; C 32.6%, H 2.7%, N 1.4%, F 48.0%.

The 'H-NMR spectrum indicated a mixture of approximately ⅔ of the desired product and ⅓ of the starting material phenol as evidenced by two different methoxy signals at 3.82 and 3.90 ppm.

EXAMPLE 11

2 g. of the product of Example 10 were mixed with 0.20 g. of Pluronic F-68 and 17.80 g. isopropanol and the mixture was warmed with stirring until all the solids dissolved. The weight of the product solution was readjusted to 20 grams by addition of isopropanol to obtain a cloudy solution containing a calculated 5.18% fluorine and 11.0% solids. 2 g. of this solution were then added to 20 cc of isopropanol and diluted to 100 ml by addition of distilled water. This diluted solution was then used as an internal fluorochemical sizing agent for paper pulp to render the same oil and water repellent, by adding 100 ml of the diluted solution to 6 g. of dry paper pulp admixed with 300 g. water.

EXAMPLE 12

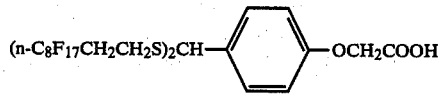

Into a 100 ml 3-neck round bottom flask, fitted with a thermometer, $N_2$ inlet, condenser and magnetic stirrer on a steam bath, 19.15 g. (0.018 moles) of a phenol corresponding to the product of Example 4 and 25.90 g. of isopropanol were added and heated to 40-45% with stirring until a yellow orange solution was obtained. To this solution were added 5.76 g. (0.072 moles) of sodium hydroxide resulting in a 5° C. exotherm. The mixture was stirred at 40°-45° C. for about ½ hour. Then 13.61 g. (0.036 moles) of 25% aqueous chloroacetic acid were added and the temperature raised to about 75° C. and held there with stirring. The color became a dark brown as the reaction proceeded, and was stirred for about 4 hours at 70°-75° C. to obtain the sodium salt of the desired product. The resulting material was stirred into 500 g. of 10% aqueous HCl for about ½ hour and the desired product in the acid form precipitated out. The product was filtered and dried for 2 days to yield a dark pink waxy solid (yield=82.29%).

Analysis of product: calc.; C 31.01%, H 1.43%, F 57.57%. found; C 29.6%, H 1.4%, F 57.3%.

EXAMPLE 13

The product of Example 12 was converted into an emulsion of the diethanolamine salt thereof by mixing 4.00 g. of the product of Example 12 in the form of its free acid with 0.67 g. of diethanolamine in the presence of 14.16 g. of water and an emulsifier, Pluronic F-68. The mixture was heated to 170°-175° F. for 10 minutes, then rolled in a jar on an automated roller overnight to obtain a slightly pinkish amber colored paste, having a theoretical solids content of 22.0% and a fluorine content of 10.1%. When diluted with water to 1.0% solids with water, the product is a cloudy solution having a pH of about 9.7. When the aforementioned amber colored paste is added in an amount of 2 g to 20 cc of isopropanol and diluted to 100 ml by addition of distilled water, the resulting product was found useful as a fluorochemical sizing agent for paper pulp to render the pulp and water repellent, by adding 100 ml of the diluted solution to 6 g of dry paper pulp admixed with 300 g. water.

EXAMPLE 14

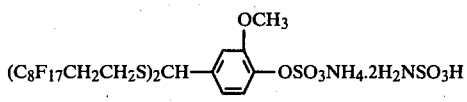

Into a 300 ml. round bottom flask fitted with a mechanical sitrrer, $N_2$ inlet, thermometer and reflux condenser, there were added 16.41 g. (0.0150 moles) of the product of Example 3, 1.60 g. (0.0165 moles) sulfamic acid, and 100 grams pyridine. The reaction mixture was stirred and heated to reflux (approx. 115° C.) for 2 hours, resulting in a clear yellow solution. After cooling to 65° C., 2.91 g. (0.030 moles) of additional sulfamic acid were added and stirred at reflux for another 1½ hours, resulting in a dark yellow solution with a small amount of precipitate. The reaction mixture was stripped down in a rotary evaporator and the resulting solids were dried further in a 50° C. vacuum oven for several hours, followed by drying until no more pyridine odor remained. 22.2 g. of a yellow wax was recovered.

Analysis of $C_{28}F_{34}H_{25}O_{11}S_5N_3$: calc.; C 24.27%, H 1.82%, N 3.03%, F 46.61%. found; C 27.6%, H 2.2%, N 4.6%, F 40.4%.

EXAMPLE 15

2.0 g. of the product of Example 14 combined with an emulsifier, Pluronic F-68, (0.20 g.) 17.80 grams of a 1:1 mixutre of distilled water and isopropanol in a 2 ounce jar. The mixture was stirred while heating to about 140°-160° F. until a solution is obtained. Then sufficient 1:1 water/isopropanol is added to obtain 20.0 grams product. The resulting product theorectically contains 11.0% solids and 3.98% fluorine. This product can be used, as is, in a manner analogous to that of Example 13, to render paper pulp both oil and water repellent.

What is claimed is:
1. A compound of the formula

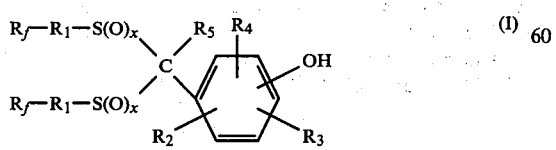

wherein
each of $R_f$ is independently straight or branched chain perfluoroalkyl of 2 to 18 carbon atoms or perfluoroalkoxy-perfluoroalkyl of 4 to 18 carbon atoms;

each $R_1$ is independently straight or branched chain alkylene of 1 to 12 carbon atoms, alkylenethioalkylene of 2 to 12 carbon atoms, alkyleneoxalkylene of 2 to 12 carbon atoms, or alkyleneiminoalkylene of 2 to 12 carbon atoms where the imino nitrogen atom contain as a third substituent hydrogen or alkyl of 1 to 6 carbon atoms;

each $R_2$, $R_3$ and $R_4$ is independently hydrogen, chloro, bromo, alkyl of 1 to 6 carbon atoms, hydroxyalkyl of 1 to 6 carbon atoms or alkoxy of 1 to 6 carbon atoms, and $R_2$ and $R_3$ additionally may, together with the carbon atoms to which they are attached, form a fused benzo ring;

$R_5$ is hydrogen or alkyl of 1 to 6 carbon atoms which is unsubstituted or substituted by hydroxy, alkoxy of 1 to 7 carbon atoms or phenyl;

x is 0, 1 or 2; and the alkali metal, alkaline earth metal, ammonium or amine phenate salt wherein the amine cation thereof is of the formula

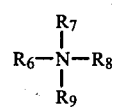

where $R_6$, $R_7$ and $R_8$ are independently hydrogen, alkyl of 1 to 5 carbon atoms, hydroxyalkyl of 2 to 5 carbon atoms, ethyleneoxyethanol or polyethyleneoxyethanol having 2 to 20 ethyleneoxy units; and $R_9$ is hydrogen, alkyl of 1 to 23 carbon atoms, hydroxyalkyl of 2 to 5 carbon atoms, phenyl, benzyl, cyclohexyl, ethyleneoxyethanol or polyethylenoxyethanol having 2 to 20 ethyleneoxy units.

2. A compound according to claim 1 which is in the form of the sodium, lithium, potassium, magnesium, calcium, strontium or barium salt thereof.

3. A compound according to claim 1, wherein
$R_f$ is perfluoroalkyl of 4 to 12 carbon atoms;
$R_1$ is alkylene of 2 to 6 carbon atoms;
$R_2$ and $R_3$ are hydrogen;
$R_4$ is hydrogen, alkyl of 1 to 4 carbon atoms or alkoxy of 1 to 4 carbon atoms;
$R_5$ is hydrogen or alkyl of 1 to 4 carbon atoms;
x is 0, 1 or 2;
and the alkali metal, alkaline earth metal, ammonium or amine phenate salts thereof.

4. A compound according to claim 1, wherein $R_f$ is perfluoroalkyl of 6 to 12 carbon atoms, $R_1$ is alkylene of 2 to 4 carbon atoms, $R_2$ and $R_3$ are hydrogen, $R_4$ is hydrogen, alkyl of 1 to 2 carbon atoms, or alkoxy of 1 to 2 carbon atoms, $R_5$ is hydrogen or alkyl of 1 to 2 carbon atoms, x is 0, 1 or 2, and the alkali metal, alkaline earth metal, ammonium or amine phenate salts thereof.

5. A compound according to claim 1, of the formula

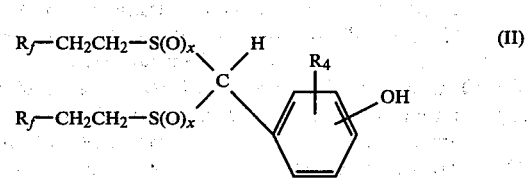

where $R_f$ is perfluoroalkyl of 6 to 12 carbon atoms, x is 0, 1 or 2, and $R_4$ is hydrogen, methyl or methoxy.
6. A compound according to claim 1, of the formula
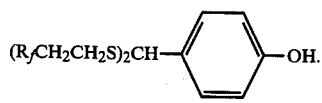
7. A compound according to claim 1, of the formula
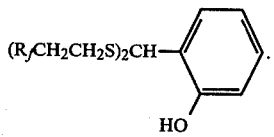
8. A compound according to claim 1, of the formula
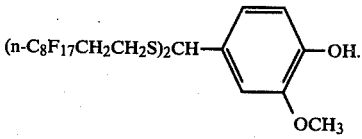
9. A compound according to claim 1, of the formula
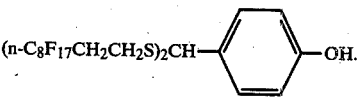
* * * * *